US 6,592,366 B2

(12) United States Patent
Triaca et al.

(10) Patent No.: US 6,592,366 B2
(45) Date of Patent: Jul. 15, 2003

(54) APPARATUS FOR PALATAL EXPANSION (75) Inventors: Albino Triaca, Germaniastrasse 47, 8006 Zurich (CH); Beat Merz, Burggartenstrasse 19, 4133 Pratteln (CH); Roger Minoretti, Moehrlistrasse 63, 8006 Zurich (CH); Thomas Egli, Ebmatingen (CH)

(73) Assignees: Albino Triaca, Zurich (CH); Beat Merz, Pratteln (CH); Roger Minoretti, Zurich (CH)

( * ) Notice: Subject to any disclaimer, the term of this patent is extended or adjusted under 35 U.S.C. 154(b) by 0 days.

(21) Appl. No.: 09/838,018

(22) Filed: Apr. 19, 2001

(65) Prior Publication Data

US 2002/0018978 A1 Feb. 14, 2002

(30) Foreign Application Priority Data

Apr. 20, 2000 (CH) .......................................... 0892/2000

(51) Int. Cl.$^7$ ................................................ A61C 3/00
(52) U.S. Cl. ........................................ 433/7; 433/173
(58) Field of Search ........................ 433/7, 173; 606/86

(56) References Cited

U.S. PATENT DOCUMENTS

| 3,977,082 | A | | 8/1976 | Siatkowski ..................... 433/7 |
| 5,620,321 | A | * | 4/1997 | Thornburg et al. ........... 433/19 |
| 5,820,369 | A | * | 10/1998 | Kvarnstrom et al. ........... 433/7 |
| 5,885,290 | A | * | 3/1999 | Guerrero et al. ............... 433/7 |
| 6,139,316 | A | * | 10/2000 | Sachdeva et al. .............. 433/7 |
| 6,302,687 | B1 | * | 10/2001 | King .............................. 433/7 |
| 6,328,745 | B1 | * | 12/2001 | Ascherman ..................... 433/7 |

FOREIGN PATENT DOCUMENTS

| EP | 0919207 | 7/1988 |
| EP | 0308645 | 3/1989 |
| WO | WO9410933 | 5/1994 |
| WO | WO9426196 | 11/1994 |

* cited by examiner

Primary Examiner—John J. Wilson
(74) Attorney, Agent, or Firm—Milde & Hoffberg, LLP (57) ABSTRACT

Apparatus for the expansion of the palate with an extension part which may be lengthened and/or shortened it its length, which has on each of its two ends a fixation part the improvement wherein each fixation part (7, 18, 30) is constructed in the form of a single-point bone connection.

17 Claims, 8 Drawing Sheets

APPARATUS FOR PALATAL EXPANSION

BACKGROUND OF THE INVENTION

The present invention relates to an apparatus for palatal expansion with an extension part which can be lengthened and shortened and having a fixation part on both ends.

Such an apparatus, also referred to as distractor, is used in maxillofacial surgery and maxillofacial orthopedics. It allows a gradual, i.e. step-wise and fast extension of the maxilla in its width or to separate two other bone segments gradually in the sense of a distraction away from each other. The apparatus may also be used in widening the maxilla in one step, in order to precisely adjust the position of the two halves of the palate relative to each other and to the mandible during surgery.

In this way congenital or acquired occlusal disturbances, malformations, bone asymmetries and pathologic relations between maxilla and mandible can be corrected.

In the first main application, the so called rapid palatal expansion, the aim is to correct an insufficient width of the maxilla by a maxillofacial surgery and orthopedics treatment such that the relation between maxillary and mandibular dentition is normalized. Thereby, the maxilla consists of a left and a right half which are united in the mid-sagittal plane in the palatal suture. In patients with an age of 12–14 years, this suture is usually not yet ossified to a great extent. Therefore the gradual separation of the two halves of the hard palate allows the orthognathic correction easily. In older juveniles or adult the suture is closed largely to completely. In these cases a surgical intervention is often necessary during which parts or the maxilla are weakened to an extent that the suture may be separated again to subsequently perform the gradual widening.

In the second main application, the conventional distraction of bone segments in an arbitrary direction, the aim is to lengthen bones in directions with insufficient length. A typical example is the too short horizontal part of the mandible which results in an overjet with the corresponding orthodontic complications and the esthetic problems with respect to the facial profile. In a surgical intervention the bone is osteotomized and bridged by the distractor. After a short initial healing phase of some days the callus forming in the osteotomy site is gradually distracted, i.e. the bone segments are moved apart by the distractor.

In a further application, such apparatus are only used during the surgery to precisely position parts of the maxilla relative to each other. A typical example is the correction of a cleft-lip-palate. This precise positioning is very difficult without such an apparatus due to the forces extorted by the soft tissues. After reaching the desired position and after controlling the occlusion with the mandible, the bone segments are fixated in the resulting position and the apparatus is subsequently removed again.

The main group of appliances used today in clinic is that where the appliances are fixated on the dentition. Therefore they have some important disadvantages.

A further option is the supporting on palatal plates. However, with those a precise guidance of the movements is very difficult due to the indirect transmission of forces via the mucosa. Below the pressure areas inflammations and hygienically problems can occur.

Known distractors of the former type which are fixated to the dentition are described for example in EP 0919207 A1, WO 94/26196 and U.S. Pat. No. 3,977,082. Distractors for palatal expansion which are based on palatal plates residing on the palatal mucosa are described in EP 0308645 A1.

Finally, WO 94/10933 describes a distractor which is based on the dentition as well as on palatal plates.

One disadvantage of the paradontal basement is the fact that the two halves of the palate may tilt in the frontal plane with the currently used designs instead of moving apart with a stable angle relation in the frontal view.

A further disadvantage of the presented state of technology is the fact that the currently available appliances enable only a single-axis, parallel displacement of the two halves of the hard palate. In the clinical application, however, it is often required to do a non-parallel widening, for instance where the posterior palate needs more expansion than the anterior. It is also important to note that the need for different vectors in the anterior and posterior palate is often only recognized during the course of treatment, because the resistance is different in the anterior and posterior.

The fixation and basement on the teeth loads the parodont which is holding the teeth in the bone. Under certain circumstances this can lead to root resorptions. Furthermore, an unwanted tilting of the teeth cannot be excluded such that eventually not the hard palate is widened but simply the dentition tilted towards lateral. Indeed, there are indications in the literature that up to 75% of the presumed movement is effectively dental rotation by nature, i.e. that the teeth have tilted or moved toward lateral which carries the danger of exposing the roots or of leading to an open bite. In adult patients with periodontal problems or lost teeth or in juveniles with congenital missing teeth a fixation to the teeth is a priori very problematic since the remaining parodont cannot transfer the forces without being harmed.

SUMMARY OF THE INVENTION

The present invention has the object to create a distractor which at least in part avoids the above mentioned disadvantages of known distractors, in particular of those which are based on fixation on the dentition.

This object is achieved by an apparatus for palatal expansion with an extenuation part which can be lengthened and shortened along its main axis and which has on both ends a fixation part characterized in that each fixation part has the form of a single-point bone connection.

By using single-point bone fixations on its extension part, such a distractor avoids palatal plates or fixation based on the dentition which would have the aforementioned disadvantages. Thereby, either special anchorage bone screws are placed through a stab incision in the palatal mucosa or the bone fixation units take the form of pins. Such bone fixation parts may be placed and fixated in more or less arbitrary positions on the bone, independent from the corresponding position of the teeth which by no means are required as fixation base for such extension parts. Also, no specific adaptations to the single patient are required as this is necessary for instance when using palatal plates or the dentition, Finally, it is also possible to fixate two distractors in predefined positions in order to extend specific force vectors to the hard palate during the palatal expansion.

It is also possible to place two independent distractors in the anterior and the posterior hard palat such that by different extension a non-parallel expansion becomes possible. Thereby the distraction axes may be placed in a way that not only a widening but also a lengthening of the palate occurs if this is necessary. In one embodiment, the bone fixation unit may be connected to the extenuation part by an adjustable in its position fixable joint. In this connection between extenuation part and bone support or screw a moment may be transferred if this is necessary by clamping the joint to the fixation unit in the one variation while it remains firm in another variation.

To limit the indention depth of the bone fixation unit into the bone and to distribute the pressure over a larger surface a thickening (enlargement) may be foreseen to limit the impression depth. Such a thickening is of advantage in screw shaped bone fixation units as well as in units with pin form.

Such a thickening which in further embodiments can take the shape of a shoulder or a rim, have the additional advantage that they may grow into the mucosa such that a form locking emerges.

Furthermore this ingrowth has the advantage that the bone fixation part is held in position and cannot drop out.

In one constructive variation of the extension part it consists of at least 3 threaded elements which screwed into each other form two counter-sense threaded pairs where turning the mid-thread element in one or the other direction results in an elongation or shortening of the extension part. Such extension parts may by very simple to elongate or shorten despite of their simple construction. Furthermore the rate of elongation or shortening per turn of the thread may be defined by the thread pitch.

In an alternative construction embodiment, the extension part is built from at least three elements. These three elements are connected with each other, whereby the first element has the form of a tube which encloses in its interior the turnable borne second element. The third element is screwed together with the second element in such a way that by turning the second element in one or the other direction the third element is pulled into or pushed out of the first element and therefore the extension part is elongated or shortened.

A construction of the distractor in a way that the axes of the bone fixation units are offset to the axis of the extension part has the advantage that also the bone fixation units can be preadjusted by corresponding fixation elements or may be readjusted. To enable this, the corresponding clamping unit may be arranged in a solvable and movable connection such that also the contained bone fixation unit can be moved together with the clamping element. In a further variation of the appliance also the clamping element is solvable and movable along the extension unit. Especially in an arrangement with axes of the bone fixation units and the extension part which are offset, a surface to exert pressure may be foreseen on the surface opposite to the actual bone connection. This in order to allow the application of a corresponding tool which could take the form a forceps which is inserted between the two opposite pressure surfaces of the bone fixation units and which can be spread such that the bone fixation units are pressed on both sides into the bone. With this construction, for instance, a rough adaptation to the bone geometry may be done, while the fine adaptation is accomplished by the help of the threads. Such a pressure surface on the bone fixation unit may take the form of a grove in order to avoid a slippage of the engaged tool.

Preferentially the joint which connects the bone fixation unit to the extension part takes the form of a ball joint, whereby the ball of the joint is part of the bone fixation unit while the extension part features a corresponding cup to receive this ball and to hold and clamp it. Mainly such a ball joint which may remain turnable or fixated by clamping in the socket enables an adaptation of the distractor such that the bone fixation units do not only move apart in a linear fashion. In one variation the ball joint between the bone fixation and the extension part is not tightened respectively temporarily released which allows the bone segments to adjust their relative angle. This, for instance, will allow the joint heads of the temporomandibular joint (TMJ) to remain in the joint socket during a mandibular midline distraction which will avoid the onset of problems in the patient's TMJs.

The previously mentioned clamping elements can be constructed such that the form one threaded element of the extension part. Thereby the corresponding threaded element of the clamping unit may be a tube with interior thread into which a threaded rod is screwed.

Further details of the invention become apparent from the following description of different design variations and the corresponding drawings.

BRIEF DESCRIPTION OF THE DRAWINGS

FIG. 6a shows a distraction in a topview of the hard palate; thereby, the distractor resides on a bone anchorage with the form of special bars, again displayed on a stone model.

FIG. 6b shows a frontal view of the left anchorage bar of FIG. 6a.

FIG. 7a shows the lateral view of a further distractor with clamping units.

FIG. 7b shows the topview of the clamping unit corresponding to view A in FIG. 7a.

DESCRIPTION OF THE PREFERRED EMBODIMENTS

The preferred embodiments of the present invention will now be described with reference to FIGS. 1–15 of the drawings. Identical elements in the various figures are designated with the same reference numerals.

Figure 1A:
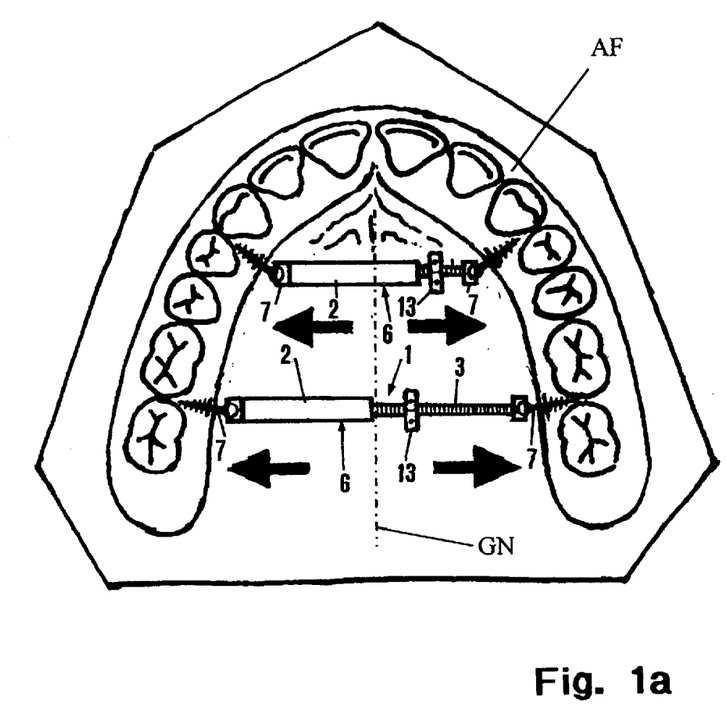
FIG. 1a shows a top view of the bony palate with 2 distractors for rapid palatal expansion where the distractors are fixated to special bone screws. The appliance is demonstrated on the base of a stone model.
Figure 1B:
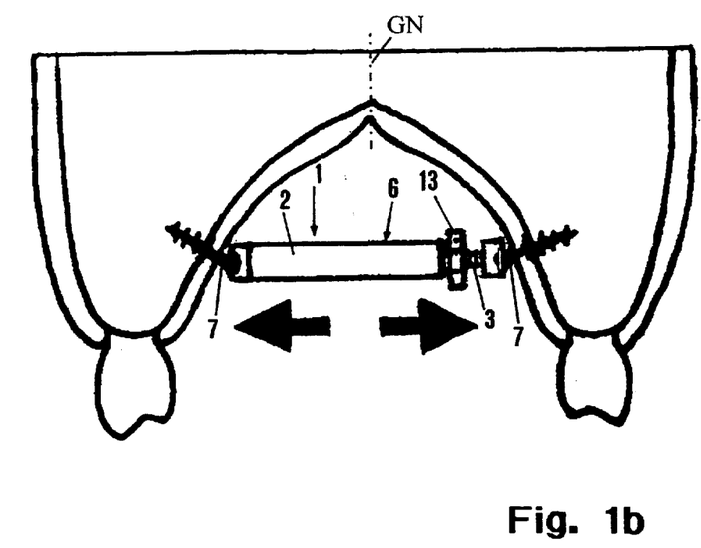
FIG. 1b shows a distractor applied to a maxilla corresponding to the embodiment of FIG. 1a in a frontal cut (again displayed applied to a stone model).

In FIG. 1a a top view on a stone model is depicted, where the anchorage of two distractors according to a first design variation is shown; thereby, one of the distractors is also shown in a frontal view in FIG. 1b.

Figures 7A, 7B:
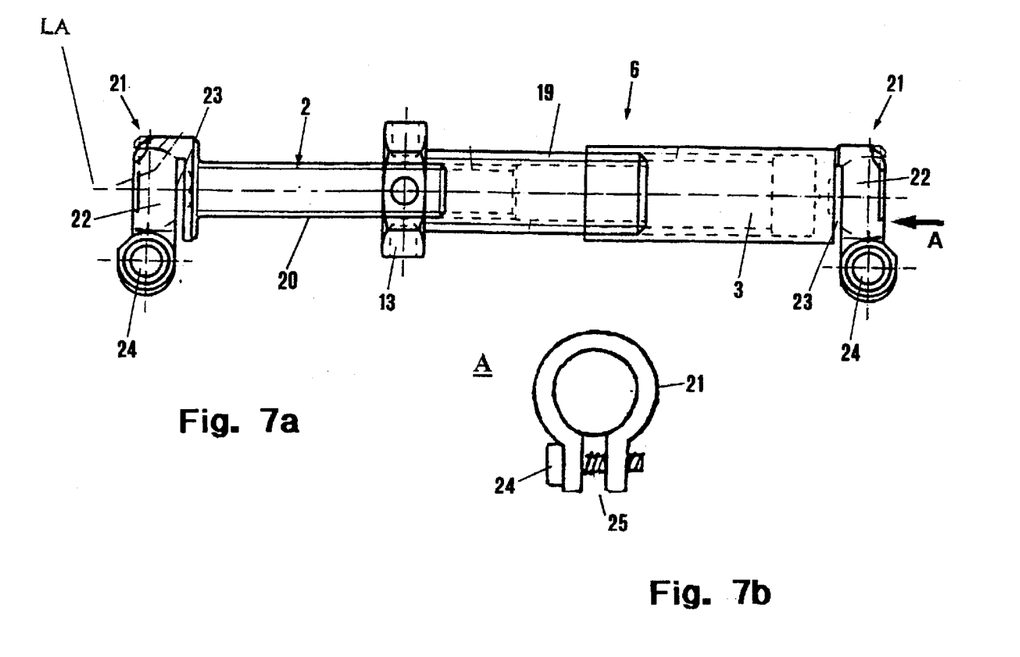

This distractor 1 which is shown more detailed in its principle design in FIG. 7a, contains two threaded elements 2, 3 where element 3 takes the form of a tube with interior thread whereas the threaded element 2 takes the form of a threaded rod. At the tip of the threaded rod 2 a joint socket 4 is fixated; a corresponding joint socket 5 is also fixated to the end of the threaded tube 3. The two threaded elements 2, 3 form an expansion part 6 which can be lengthened or shortened in its longitudinal dimensions. In the corresponding joint sockets 4, 5 at the tips of the extension unit 6 a bone anchorage part is fixated in the form of a bone screw 7. Such a bone screw 7 is shown in an enlarged view. It includes a threaded part 8 which is limited with a ring or a shoulder or disc 9. This shoulder 9 is followed by a neck 10 which again is followed by a joint ball 11. In the top portion of the joint ball 11 there is a slot or cross-slot 12 (or interior facets) to insert this bone screw 7 with a standard surgical screwdriver into the bone, as it is shown if FIGS. 1a and 1b. The shoulder 9 thereby limits the possible indention of the bone screw 7. The neck part 10 serves for bridging the mucosa such that the ball 11 is well accessible outside of the mucosa.

A first application of the distractor 1 is the fast transversal expansion of the palatal suture which is marked with GN in FIGS. 1a and 1b. For this application two distractors, as shown in FIG. 1a, are inserted in the anterior and the posterior part of the palatal respectively and fixated to the bone screws 7 which were inserted between the dental roots. The corresponding extension parts 6 of the two distractors are then elongated by turning the threaded element respectively the threaded rod 3 by the help of a hexagon nut 13 fixated to it. In this way the threaded rod 3 is turned out of the interior thread of the tube-like threaded element 2. This distraction with two distractors allows a non-parallel expansion of the palatal, in order to adapt the maxillary alveolar process (denoted with AF) with the contained teeth exactly to the mandibular dentition. In simpler cases the palatal expansion can be done with only one distractor.

Figure 2:
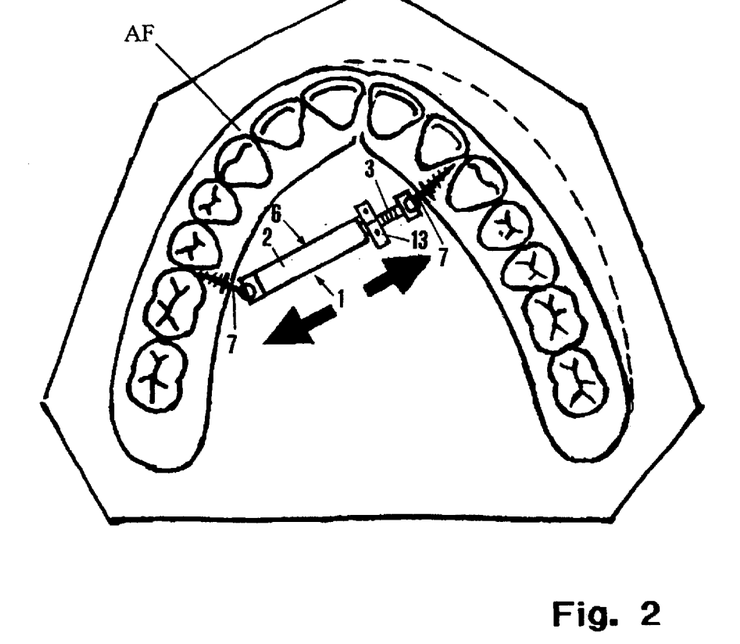
FIG. 2 shows the stone model of an asymmetric maxilla which is brought into the normal shape by an oblique distraction of a part of the alveolar process; thereby, the distractor is applied for a precise intra-operative positioning of the bone segments.

In FIG. 2 the application of distractor 1 which is shown also in FIGS. 1a and 1b is demonstrated in oblique position in the palatal on a stone model. This positioning might help to correct an asymmetry of the alveolar process (AF) of the maxilla, e.g. resulting form a cleft-lip-palatal, and to bring the deformed part of the alveolar process during surgery against the tension of the soft tissues in the correct position. The elongation of the distractor is continued until the bone segments are brought into the correct occlusion. Thereafter, the bone segments are fixated against each other with corresponding plates and screws which are not depicted.

Figure 3:
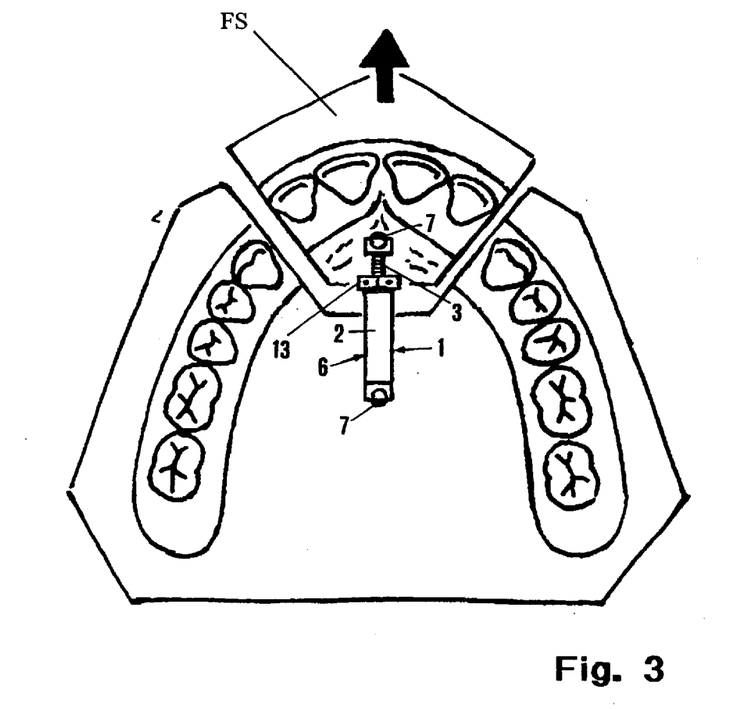
FIG. 3 shows the anterior distraction of a maxillary segment including the corresponding teeth on a stone model.

FIG. 3 shows the application of a single distractor to gradually advance a front segment (FS) of the maxilla, for instance to correct an inappropriate relation between maxillary and mandibular dentition or to resolve a frontal crowding where the teeth are turned or otherwise mal-positioned due to a lack of space. With the gradual distraction of the frontal dentate segment, additional bone is generated into which the misplaced teeth can be moved with orthodontic methods in order to resolve the frontal crowding. In this applications one bone screw is inserted into the frontal segment (FS) while the other is located in the suture of the posterior hard palatal.

Figure 4:
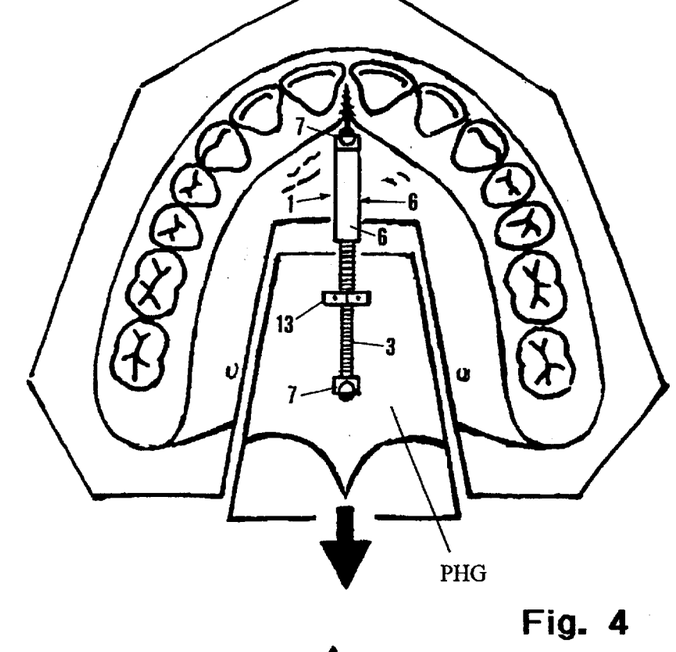
FIG. 4 shows the distraction of a segment of the posterior hard palate toward dorsal, again demonstrated on a stone model.

In the application demonstrated on the stone model shown in FIG. 4 the posterior part of the hard palatal (denoted with PHG) is distracted towards posterior as indicated by the arrow. This may be required in the case of a congenital velopharyngeal incompetence which may often be the case with cleft-lip-palatal patients. This problem handicaps the patient in talking. By the gradual posterior distraction of the posterior hard palatal this problem may be corrected in suitable cases. The arrangement of the distractor 1 is thereby chosen according FIG. 3.

Figure 5:
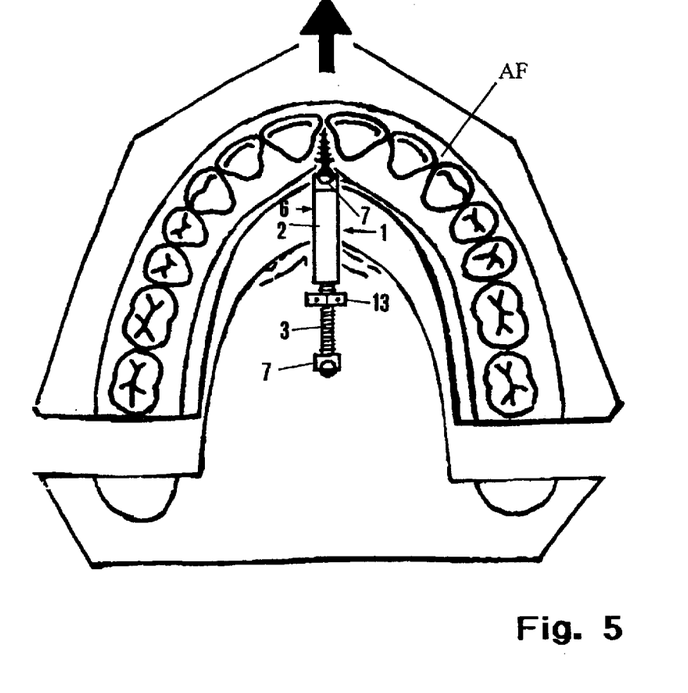
FIG. 5 shows, the distraction of a maxillary alveolar process towards anterior, displayed on a stone model.

In contrast to FIG. 4, FIG. 5 shows the gradual advancement of virtually the entire alveolar process (AF) by the distractor 1 in order to correct a mal-positioning between maxillary and mandibular dentition.

Figures 6A, 6B:
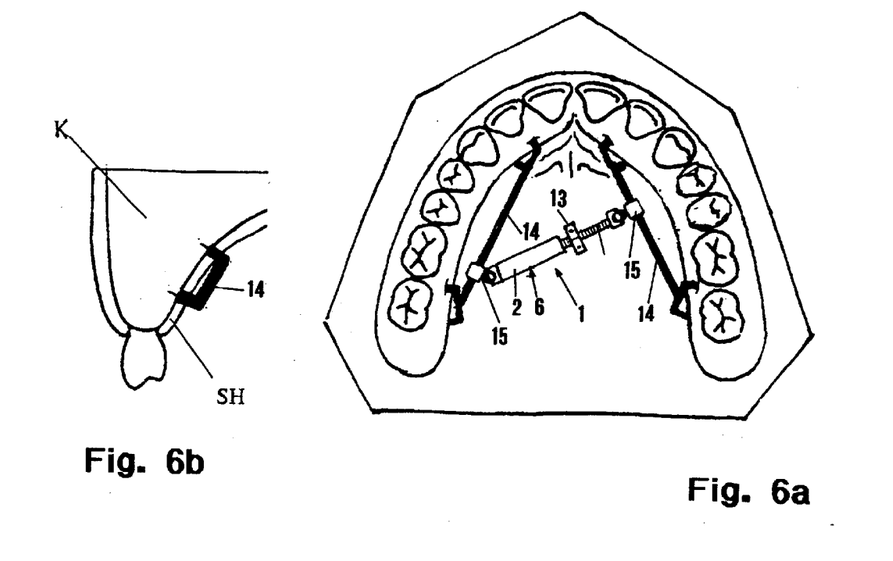

In FIG. 6a a single distractor 1 is used to widen the maxilla. Thereby the distractor is not residing on bone screws 7 with ball head but two bars 14 are inserted. Such a bar is also depicted in an enlargement in FIG. 9. The connection to distractor 1 respectively between extension part 6 and bar 14 is done by the help of connective elements 15 (see FIG. 6a) which can be fixated to the bar 16 in arbitrary position by clamping and which feature the same ball as the joint ball 11 of bone screw 7 (see FIG. 8) such that the extension part 6 may be applied in a compatible way. As shown in FIG. 9, the bar 14 includes on both ends of the bar connector 16 two U-shaped elements 17 which feature a pin 18 on both free ends. The pin 18 is smaller in diameter at its base than the frontal surface 19 of the two ends of the U-shaped element 17, such that a step is resulting which limits the indention of the bar into the bone. Furthermore, FIG. 9 demonstrates that the bar connector 16 is made of two parts connected by a thread or a simple gliding connection such that both halves can be turned against each other in order to lengthen the bar connector 16 and to adapt it to the corresponding anatomy.

The extension parts 6 as applied in FIGS. 1 to 6 are shown in an enlarged and more detailed picture in FIGS. 7a and 7b. As mentioned before, the extension part 6 of distractor 1 is made of a combination of interacting rods and tubes 2, 3 with interior and/or exterior threads. In contrast to the extension part 6 as described above, the detailed depiction in FIG. 7a shows the threaded rod 3 one more times split into a tube-like part 19 and a rod-like part 20, such that by corresponding screwing of the rod part 20 into the tube part 19 a basic elongation of the extension part 6 may be achieved. Therefore the rod part 20 has an exterior thread which engages the tube part 19 with its interior thread. The tubular part 19 features at the same time an exterior thread which interacts with the tubular threaded element 2 with its interior thread. The two thread pairs of part 20/19 and 19/2 are constructed with contrary thread direction such that turning the middle part 19 by the help of a hexagon nut 13 the whole extension part 6 is either shortened or expanded. The connection of the extension part 6 with the bone screws 7 with its joint ball 11 is done by the help of the clamping unit 21. Such as clamping unit 21 as is shown in FIG. 7b which shows a view in direction A of FIG. 7a, forms a ball-shaped concave part 22 in form of a joint socket which can hold the joint ball 11 in such a way that it snaps in when pressed into the socket. The required elasticity to clamp the joint ball 11 is achieved by including a slot 23 in orthogonal direction to the long axis (denoted as LA) of the extension part 6. The actual clamping is achieved by a screw-type connection 24 which can compress a slot 25 of the clamping unit 21 in order to clamp the joint ball 11.

Figure 10:
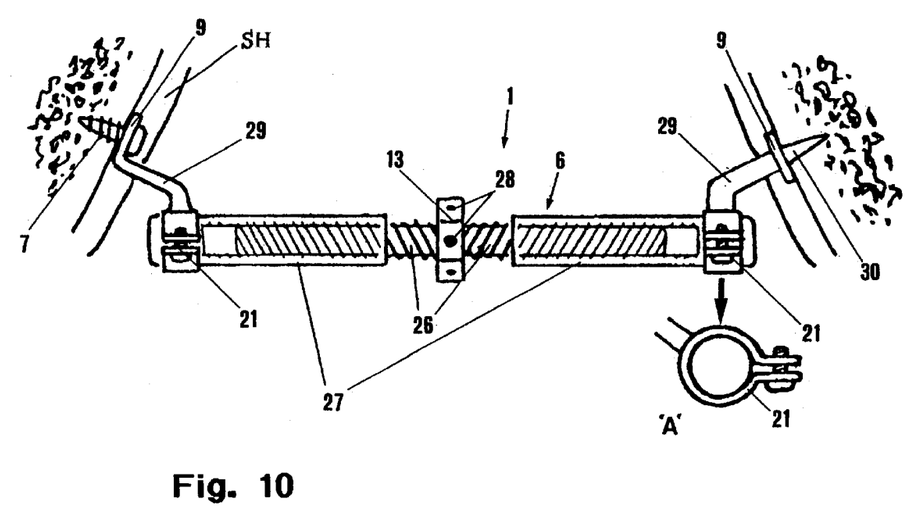
FIG. 10 shows a further variation of a distractor with special bone pins or bone plates for anchorage on the bone.

FIG. 10 shows a further variation of the distractor where in this depiction of possibilities of bone connection a shown. In this construction, the extension part 6 features a threaded rod with two counter running threads 26, between both of which a hexagon nut 13 is included in order to rotate the threaded rod. On each of the two counter running threads 26 is tube with the corresponding interior thread 27 is mounted. By turning the hexagon nut 13 one or the other direction, the extension part is elongated or contracted. As depicted in FIG. 10, the hexagon nut has radial holes 28 in which a tool can be inserted in order to turn it. On the outer side of the two tubes 27 a clamping unit 21 is mounted, which corresponds in its basic design to the clamping unit as depicted in FIG. 7b. From this clamping unit 21 an arm 29 emerges which is angled and features either a bone plate 9a for There has thus been shown and described a novel apparatus for palatal expansion which fulfills all the objects and advantages sought therefor. Many changes, modifications, variations and other uses and applications of the subject invention will, however, become apparent to those skilled in the art after considering this specification and the accompanying drawings which disclose the preferred embodiments thereof. All such changes, modifications, variations and other uses and applications which do not depart from the spirit and scope of the invention are deemed to be covered by the invention, which is to be limited only by the claims which follow. one or more standard bone screws 7 (left side) or a pin 30 (right side) with shoulder 9 to limit the indention depth of the bone connection. In FIG. 10 the mucosa in marked with SH. The bone screw 7 is inserted into the bone through a stab incision of the mucosa SH as indicated in FIG. 10. The arms 29 are angled such that the bone screw 7 respectively the pin 30 can be inserted in orthogonal direction to the corresponding bone surface of the hard palatal. The flexibility and adaptability to the individual bone topography is strongly improved by the fact that the arm 29 can be clamped to the extension part 6 in arbitrary position and angle about the long axis thanks to the clamping unit 21.

Figure 8:
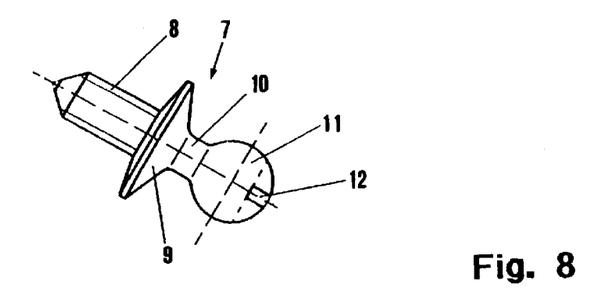
FIG. 8 shows an enlarged view of a ball head screws
Figure 9:
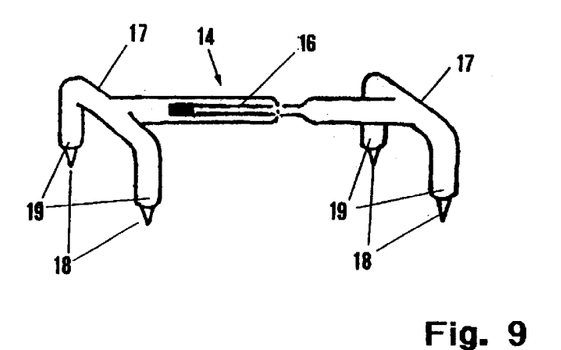
FIG. 9 shows an enlarged view of an anchorage bar.

The use of arms 29 with bone plates 9a is of special advantage in the case of thin bone where the special screws 2 according to FIG. 8 do not find sufficient material for a stable anchoring.

Furthermore, the flexible positioning of the pin or the bone screws outside of the direct long axis of the distractor makes more place available for it in case of the often narrow palatal arches since it can be placed virtually onto the mucosa.

It is to be noted that the parts which are comparable with respect to their function in the different design variation are marked with corresponding reference numbers in the single figures such that the explanation to the single figures can analogously be transferred to the other figures.

Figure 11A:
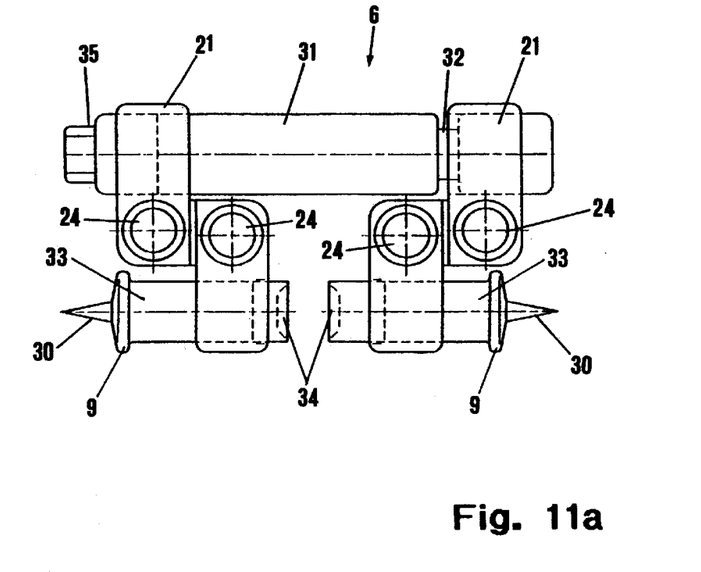
FIGS. 11a and 11b show the lateral view of a further distractor in a contracted and an expanded position.
Figure 11B:
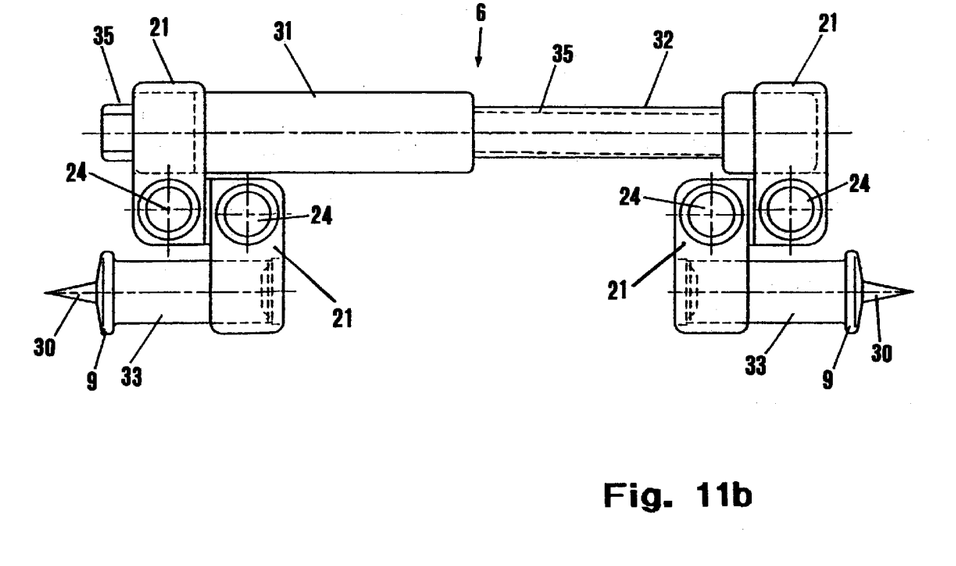

FIGS. 11a and 11b show a further design variation of a distractor with a three-part extension unit 6 with a cylindrical tube 31, with a elongation part 32 and a threaded element 35 guided in one of the tubular parts 31 which features at its left, prominent end a multi-faceted exterior contour to turn this threaded element by the help of these exterior facets. This threaded element 35 is screwed into the elongation part 32 which has an interior thread which is evident from the broken lines, such that by turning the faceted part the elongation part 32 is moving out of the tubular part 31, i.e. is elongated, or moving into the tubular part 31, i.e. contracted. The tubular part 31 is secured against rotating; the same is true for the elongation part 32.

On the respective ends of tube 31 and threaded bolt 32 clamping units 21 are fixated which can be clamped by the help of the screw connections 24. A second clamping unit 21 is connected to the first clamping unit 21 by a fitting connection and may be clamped to this connection by the help of the screw connection 24. In this second clamping unit 21 a pin 30 is fixated which has a cylindrical elongation 32. The cylindrical elongation 33 may be clamped to the corresponding clamping unit 21 in a desired position such that the extension part 6 may additionally be adapted in its length by the help of this cylindrical elongation part 33.

FIG. 11a shows the distractor in a contracted position with the smallest possible dimension in direction of its long axis, while FIG. 11b shows it in its maximally elongated position. As can be seen in FIG. 11a, the frontal ends of the cylindrical elongation parts 33 which are opposite to the pin 30 feature a concave grove 34. In these two groves 34 of the opposite cylindrical elongation parts 33 a tool, for instance in the form of a forceps, may be engaged in order to press the two cylindrical elongation parts 33 apart and to anchor the corresponding pins 30 into the bone at a desired position, all before the extension part is elongated by turning the threaded bolt 32.

In this design variation the axes of the extension part (parts 31, 32 and 35) are displaced to the axes of the cylindrical elongation parts 33 such that a design results where the extension part 6 is displaced compared to the bone anchoring points.

Figure 12A:
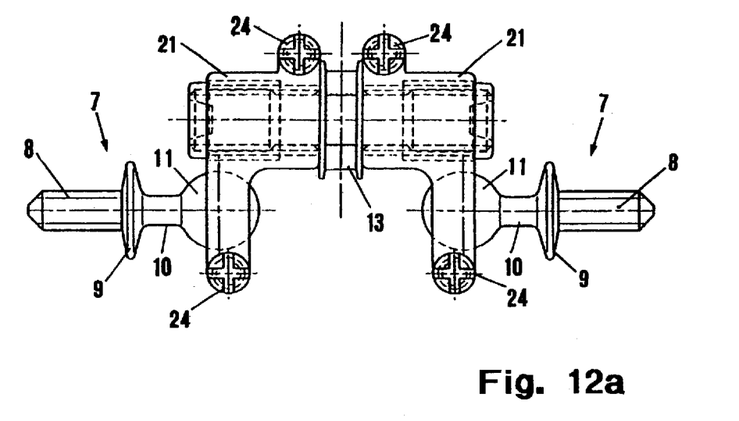
FIGS. 12a and 12b show a further variation of a distractor in the two different positions corresponding to those in FIGS. 11a and 11b.
Figure 12B:
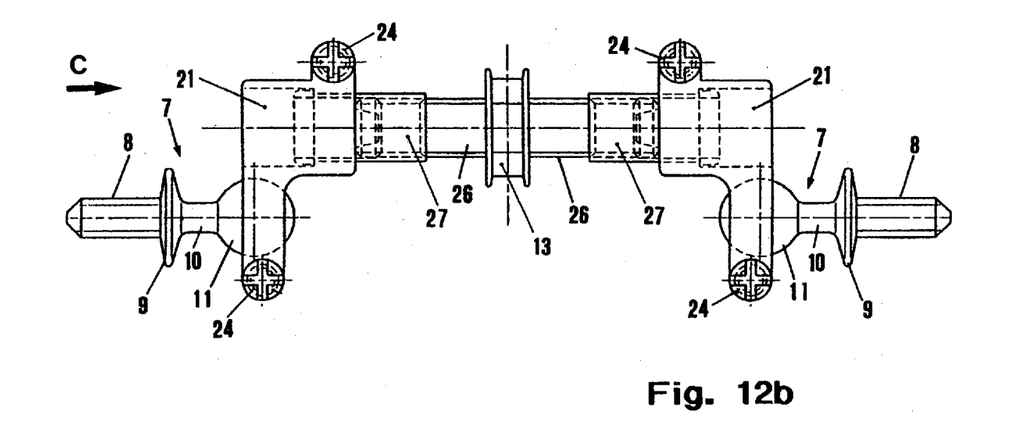
Figure 12C:
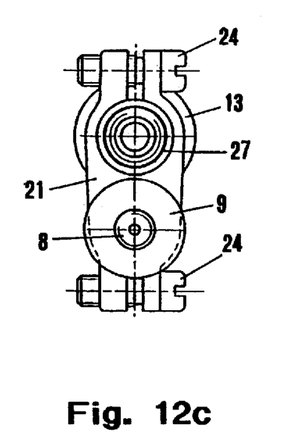
FIG. 12c shows a top view of the arrangement in FIG. 12b from the view direction C.

In FIGS. 12a to 12c a further distractor is shown which in its basic design corresponds to the distractor depicted in FIG. 10. The clamping units 21 are in comparison to the design in FIG. 10 designed is such a way that they can receive the joint ball 11 of a bone screw 7 as depicted in FIG. 8 according to the construction as shown in FIG. 7a. However, due to the special clamping units 21 in this example the axes of the extension part 6 and the bone screws 7 are displaced against each other. Furthermore, the clamping units 21 may be moved and fixated on the tubes 27 by the help of the corresponding clamping screws 36 which is evident from the different positioning of the clamping units 21 in FIGS. 12a and 12b. The corresponding tube 27 and the corresponding clamping unit 21 are connected to each other by form lock such that the clamping unit 21 cannot fall of the tube 27.

Figure 13:
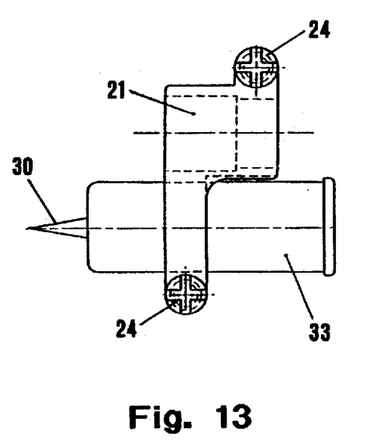
FIG. 13 shows a clamping unit as shown in FIGS. 12a and 12b; in this embodiment the anchorage part with a ball and a threaded element is replaced by a pin-like anchorage which is slidable within the clamping unit.

FIG. 13 shows the clamping unit 21 as it is used in FIGS. 12a and 12b but in this case with a pin 30 and a cylindrical elongation part 33, corresponding to the design variation in FIG. 11b which can be used in lieu of the bone screw 7 of FIGS. 12a and 12b if the distractor is not to be screwed into the bone.

Figure 14A:
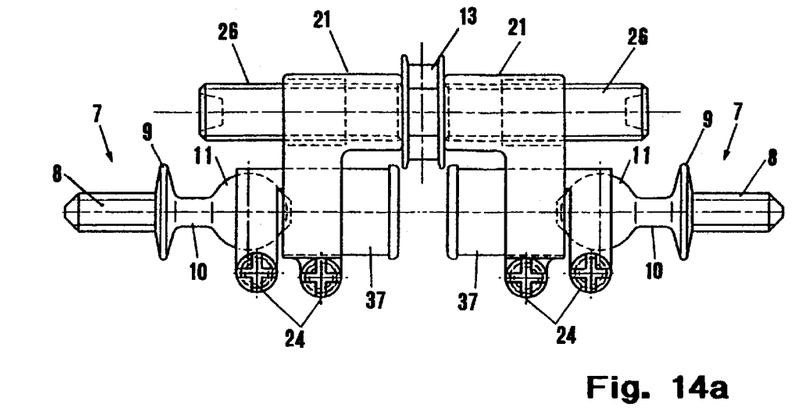
FIGS. 14a, 14b and 14c show a further arrangement which is comparable to that in FIGS. 12a, 12b and 12c.
Figure 14B:
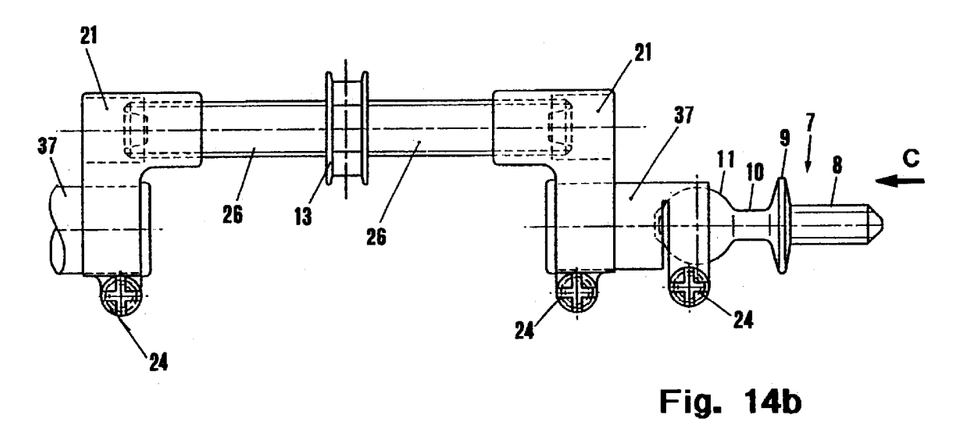
Figure 14C:
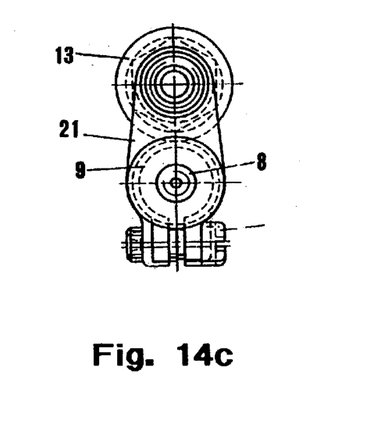

In the design variation of FIGS. 14 to 14c the clamping units 21 with their corresponding internal threads are positioned immediately onto the threaded bolt 26 on both sides of the hexagon nut 13 with their counter running external threads. Otherwise, these clamping units correspond to those which are shown in FIG. 13 where, however, a specific cylindrical elongation element 37 is included in the clamping units 21, which features a clamping part on its lateral end in order to hold there a ball joint 11 of a bone screws. The construction of this clamping part corresponds to the one as it is found on both ends of extension part 6 in FIG. 7a.

Figure 15:
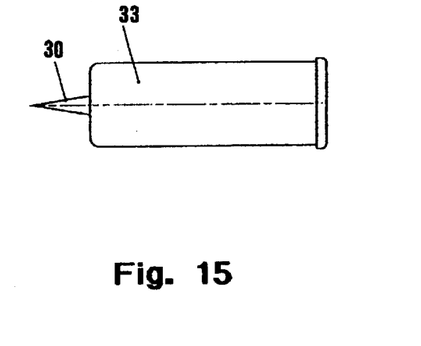
FIG. 15 shows a clampable pin which can be placed instead of the screwable clamping units with ball head in the variation of FIGS. 14a and 14b.

Instead of the cylindrical elongation element 37 a cylindrical elongation part 33 with pin 30 may as shown in FIG. 15 may be inserted such that with this construction a large variability of the distractor is given.

The distractors as shown in FIGS. 11, 12 and 14 have as a common feature the displaced axes of extension part 6 relative to the axes of the bone connection elements in form of bone screws 7 or the pins 30.

What is claimed is:

1. Apparatus for the expansion of the palate with an extension part which may be lengthened and/or shortened in its length, and which has a fixation part on each of its two ends, the improvement wherein each fixation part is constructed in the form of a single-point bone connection; wherein longitudinal axes of said bone connections are offset with respect to a longitudinal axis of the extension part; and wherein each of said bone connections is held on the extension part by a clamping part.

2. Apparatus according to claim 1, wherein said bone connection is connected to the extension part by an adjustable joint which is fixable in its position.

3. Apparatus according to claim 2, wherein the joint is in the form of a ball joint, and wherein a ball of the ball joint is part of the bone connection.

4. Apparatus according to claim 3, wherein the ball may be a cup and a clamping screw for holding and clamping said ball, respectively, and wherein said ball may be clamped in said cup by tightening said clamping screw or may remain rotatable by loosening the clamping screw.

5. Apparatus according to claim 1, wherein said bone connection is in the form of a bone screw.

6. Apparatus according to claim 1, wherein said bone connection is in the form of a pin.

7. Apparatus according to claim 1, wherein said bone connection comprises a shoulder limiting the depth of impression of the bone connection into palate bone.

8. Apparatus according to claim 7, wherein said shoulder is in the form of a disk.

9. Apparatus according to claim 7, wherein said shoulder is in the form of a rim.

10. Apparatus according to claim 1, wherein said extension part comprises at least three threaded elements which form, when screwed into each other, two counter running pairs of threads, and wherein turning a middle threaded element in the one or the other direction causes lengthening or shortening of the extension part.

11. Apparatus according to claim 10, wherein each of said bone connection is held on the extension part by a clamping part, and wherein two of the threaded elements are formed by portions of the two clamping parts.

12. Apparatus according to claim 11, wherein the corresponding threaded element of the clamping part is in the form of a tube with interior threads.

13. Apparatus according to claim 1, wherein said extension part comprises at least three elements which are connected to each other, wherein a first element is in the form of a tube which receives a second element, and wherein a third element is screwed to the second element in such a way that the third element, by turning the second element in one or an opposite direction, is pulled into the first element or pressed out of it, whereby the extension part is lengthened or shortened.

14. Apparatus according to claim 1, wherein the clamping part is detachable and movable with respect to said extension part.

15. Apparatus according to claim 1, wherein said bone connection is fixed to its respective clamping part in a detachable and movable connection.

16. Apparatus according to claim 1, wherein the bone connection has a surface for pressure application on its end, opposite to a bone contact portion thereof.

17. Apparatus according to claim 16, wherein the surface for pressure application is in the form of a groove.

* * * * *